(12) United States Patent
Lee et al.

(10) Patent No.: US 10,350,156 B2
(45) Date of Patent: Jul. 16, 2019

(54) **METHOD FOR PREPARING COSMETIC COMPOSITION CONTAINING FERMENTED GINSENG BERRY *PLEUROTUS FERULAE* PRODUCT AND USE THEREOF**

(71) Applicant: AMI COSMETIC CO., LTD., Seoul (KR)

(72) Inventors: Kyung Rok Lee, Seoul (KR); Il Hong, Seoul (KR); Do Gyeong Lee, Gyeongsanbuk-do (KR); Sung Min Park, Chungcheongbuk-do (KR); Jung No Lee, Chungcheongbuk-do (KR); Nu Rim Lee, Jeollanam-do (KR)

(73) Assignee: AMI COSMETIC CO., LTD., Seoul (KR)

( * ) Notice: Subject to any disclaimer, the term of this patent is extended or adjusted under 35 U.S.C. 154(b) by 568 days.

(21) Appl. No.: 15/016,495

(22) Filed: Feb. 5, 2016

(65) Prior Publication Data

US 2016/0151273 A1 Jun. 2, 2016

Related U.S. Application Data

(63) Continuation of application No. 14/250,136, filed on Apr. 10, 2014.

(30) Foreign Application Priority Data

Oct. 11, 2013 (KR) .......................... 10-2013-0120984

(51) Int. Cl.
| | |
|---|---|
| *A61K 36/258* | (2006.01) |
| *A61K 36/07* | (2006.01) |
| *A61K 8/97* | (2017.01) |
| *A61Q 19/00* | (2006.01) |
| *A61Q 19/02* | (2006.01) |
| *A61Q 19/08* | (2006.01) |
| *C12P 1/02* | (2006.01) |
| *A61K 8/9706* | (2017.01) |

(52) U.S. Cl.
CPC .............. *A61K 8/97* (2013.01); *A61K 8/9706* (2017.08); *A61Q 19/00* (2013.01); *A61Q 19/02* (2013.01); *A61Q 19/08* (2013.01); *C12P 1/02* (2013.01); *A61K 2800/522* (2013.01); *A61K 2800/85* (2013.01)

(58) Field of Classification Search
None
See application file for complete search history.

*Primary Examiner* — Christopher R Tate
*Assistant Examiner* — Russell G Fiebig
(74) *Attorney, Agent, or Firm* — Vorys, Sater, Seymour & Pease LLP; Minh Suhn Koh

(57) ABSTRACT

Disclosed are a fermented ginseng berry *Pleurotus ferulae* product and a cosmetic composition containing the same. The fermented ginseng berry *Pleurotus ferulae* product is useful for anti-oxidation, anti-inflammation, collagen synthesis facilitation, skin wrinkle care, whitening, moisturizing, skin barrier improvement and atopy alleviation.

6 Claims, 5 Drawing Sheets

METHOD FOR PREPARING COSMETIC COMPOSITION CONTAINING FERMENTED GINSENG BERRY *PLEUROTUS FERULAE* PRODUCT AND USE THEREOF

CROSS-REFERENCE TO RELATED APPLICATION

This application is a Continuation of U.S. patent application Ser. No. 14/250,136 filed on Apr. 10, 2014, which claims priority to Korean Application No. 10-2013-0120984 filed on Oct. 11, 2013, which are incorporated herein by reference.

TECHNICAL BACKGROUND

The present invention relates to a cosmetic composition containing, as an active ingredient, a fermented ginseng berry *Pleurotus ferulae* product. More specifically, the present invention relates to a cosmetic composition containing, as an active ingredient, a fermented product prepared by fermenting a ginseng berry extract with *Pleurotus ferulae* mycelium.

RELATED ART

Aging of the skin is classified into two types, i.e., intrinsic (chronological) aging and photoaging [Gilchrest B A: *J. Am. Acad. Dermatol.*, 21, 610-613 (1989)]. Intrinsic aging naturally occurs due to decrease in physiologic functions with age [Braverman I M, et al.: *J. Invest. Dermatol.*, 78, 434-443 (1982)]. Photoaging means change associated with appearance and functions of the skin, caused by repeated exposure of the skin to solar radiation [Ridder G M et al.: *J. Am. Acad. Dermatol.*, 25, 751-760 (1991)]. In addition, aging of the skin may be caused by ultraviolet radiation, stress, disease conditions, environmental factors, wounds and activation of active oxygen species with age. As such conditions worsen, antioxidant defense mechanisms present in vivo are destructed, cells and tissues are damaged, and adult diseases and aging are facilitated. More specifically, oxidation of lipids, proteins, polysaccharides, nucleic acids and the like, which are primary components of the skin, and destruction of skin cells and tissues thus causes aging of the skin. In particular, oxidation of proteins involves cleavage of collagen, hyaluronic acid, elastin, proteoglycan, fibronetin and the like, which are connective tissues of the skin, results in over-inflammation, causes damage to elasticity of the skin and, in serious cases, brings about mutations caused by DNA modification, emergence of cancers and deterioration in immune function.

Accordingly, it is necessary to protect the skin through scavenging of active oxygen species produced during in vivo metabolic processes or active oxygen species mediated by ultraviolet irradiation and inflammation, and to degenerate and proliferate damaged cells through active metabolism so as to restore the skin and keep the skin healthy. An enzyme called "matrix metalloproteinase (MMP)" as well as active oxygen species is mediated in aging. Synthesis and decomposition of the extracellular matrix such as collagen are suitably controlled in vivo, but the synthesis is deteriorated with aging, expression of collagenase, i.e., matrix metalloproteinase (MMP) is facilitated, elasticity of the skin is deteriorated and wrinkles are created. In addition, exposure to ultraviolet radiation may cause activation of such a decomposition enzyme. Thus, there is a demand for development of substances which control expression of MMP activated in cells by ultraviolet radiation or inhibit the activity of MMP. Most ingredients used as raw materials of cosmetics to date simply inhibit only activity of matrix metalloproteinases (MMPs).

Meanwhile, melanin is produced through conversion of tyrosine into dopa, dopaquinone and then dopachrome by actions of tyrosinase present in pigment cells. Melanin is present in the skin, which protects the body from ultraviolet radiation and has an essential function on control of hormone secretion in vivo. However, over-production of melanin is known to create spots, freckles and the like, accelerate aging of the skin and play an important role in inducing skin cancers. As such, research and development to prevent melanin over-production is actively underway. Ascorbic acid (Japanese Patent Publication Sho. 4-9320), hydroquinone (Japanese Patent Publication Sho. 6-192062), kojic acid (Japanese Patent Publication Hei. 56-7710), arbutin (Japanese Patent Publication Sho. 4-93150), plant extracts and the like have already been used for whitening cosmetics owing to inhibitory activity against tyrosinase, but use thereof is limited due to problems such as decomposition and discoloration caused by bad stability in cosmetic formulations, generation of off-flavor, unclear in vivo efficacies and effects, and safety.

Meanwhile, human skin is an organ which serves as a protective membrane which protects human from external environments, and functions to prevent loss of biogenic substances such as water and electrolytes and prevent harmful substances from invading into the human. Skin is broadly divided into the epidermis, the dermis and subcutaneous fat. The epidermis is composed of keratinocytes and melanocytes. A keratinocyte layer which constitutes the outermost layer of the skin directly contacts external environments and thus should have high physical or chemical resistance or superior barrier property to materials, prevent release (loss) of water to the outside from the human, and maintain flexibility due to presence of a proper amount of water therein.

In general, content of water in the skin is about 70% for the dermis, but content of water gradually decreases from the dermis to the epidermis and the keratinocyte layer. The content of water in the keratinocyte layer is about 10% to about 30%. The water supplied from the dermis is predominantly moved to an upper part of the keratinocyte layer via passive diffusion and is finally discharged to the outside. This phenomenon is referred to as a "trans-epidermal water loss (TEWL)" and lipid membranes, i.e., sebum and cuticular lipids, of the keratinocyte layer, are known to regulate such TEWL to a proper level.

Meanwhile, a hydrophilic substance capable of retaining water, called "natural moisturizing factor (NMF)", present in the keratinocyte layer is known to play an important role in moisturizing the skin. When a normal keratinocyte layer maintains a water content of about 10 to about 30%, the skin becomes smooth and soft and normally exerts the function of protecting the body. However, when the water content of the keratinocyte layer is 10% or less, the skin becomes rough, losses its body protection function and is aged. For example, in the case of the dry skin, a scaling phenomenon in which scale-like keratinocytes are peeled off the surface of the skin due to weak adhesion between keratinocytes occurs. The dryness of the skin is due to the fact that the dry skin has a water content of the keratinocyte layer lower than that of normal skin. In addition, even healthy skin has bad conditions due to lack of water caused by exposure to harsh external environments, i.e., wind, cold weather, sunlight, washing or shaving.

Accordingly, it is considerably important to suitably maintain a water content of the skin keratinocyte layer. For this purpose, cosmetics containing components similar to sebum, NMF components or moisturizers such as polyols were used. For example, glycerin or sorbitol having three or more hydroxyl groups (OH groups), as water-soluble polyols, exhibit excellent moisturizing effect, but renders discomfort upon use due to severe stickiness, and propylene glycol, 1,3-butylene glycol and the like having two hydroxyl groups (OH groups) cause side effects to the skin. In addition, other natural moisturizing factors such as pyrrolidone carboxylate sodium (PCA-Na), sodium lactate and urea have a problem of impairing emulsion stability due to high electrolytic property. Amino acids, collagen, elastin and the like have moisturizing properties, but the moisturizing properties thereof are limited.

The water retention property of the keratinocyte layer may be controlled by natural moisturizing factors (NMFs) composed of amino acids, lactic acid, urea and inorganic salts. Development of substances for external application to the skin, which are safe, and have excellent usability and superior moisturizing effects like natural moisturizing factors, is an important research issue in cosmetics.

On the other hand, in recent years, cosmetics using natural substances are used to reduce skin irritation caused by chemicals. A development value of natural substances as raw materials for cosmetics is gradually increased because the natural substances reduce side effects in the skin and the response of recent cosmetic consumers to cosmetics using natural ingredients is increased.

As a result of research into applicability of a variety of natural substances to cosmetics, the inventors of the present invention discovered that an extract of ginseng berries prepared by fermentation with *Pleurotus ferulae* mycelium exhibits anti-oxidation, anti-inflammation, collagen synthesis promotion, skin wrinkle care, whitening, moisturizing, skin barrier function and atopy alleviation effects. The present invention was completed based on this discovery.

(Patent Document) Korean Patent No. 10-0887631 (registered on Mar. 2, 2009) discloses a composition for external application to the skin containing a ginseng berry extract and a cosmetic containing the ginseng berry extract as an active ingredient.

SUMMARY OF THE INVENTION

Therefore, the present invention has been made in view of the above problems, and it is an object of the present invention to develop and provide a cosmetic composition using a ginseng berry which is applicable to skin cosmetics and has considerably safety due to non-harmness to the human body.

In accordance with the present invention, the above and other objects can be accomplished by the provision of a cosmetic composition containing, as an active ingredient, a fermented ginseng berry *Pleurotus ferulae* product obtained by fermenting a ginseng berry extract with *Pleurotus ferulae*.

Meanwhile, the cosmetic composition of the present invention is for example used for any one selected from anti-oxidation, anti-inflammation, skin wrinkle care, skin whitening, skin moisturizing and atopy alleviation.

Meanwhile, in the cosmetic composition according to the present invention, the ginseng berry extract is for example extracted using any one extraction solvent selected from the group consisting of water, C1-C4 anhydrous or aqueous lower alcohol, acetone, ethyl acetate, butyl acetate and 1,3-butylene glycol.

Meanwhile, regarding the cosmetic composition according to the present invention, the fermented ginseng berry *Pleurotus ferulae* product is preferably present in an amount of 0.0001 to 100.0% by weight, with respect to the total weight of the cosmetic composition.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
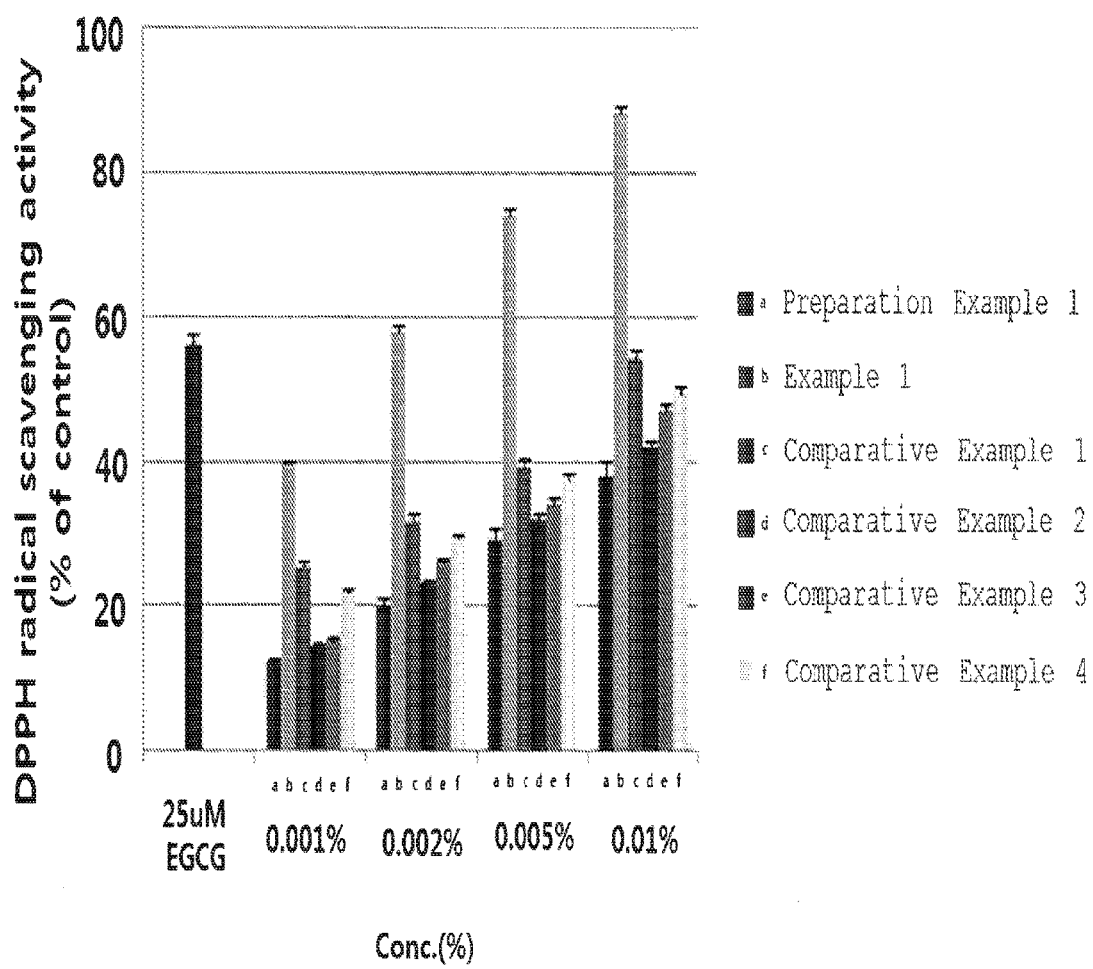
FIG. 1 is a graph showing comparison in free radical scavenging activity at different concentrations (0.001%, 0.002%, 0.005%, 0.01%) between a ginseng berry extract obtained in Preparation Example 1 and fermented ginseng berry products obtained in Example 1 and Comparative Examples 1 to 4, wherein 'EGCG' represents epigallocatechin gallate, 'a' represents a ginseng berry extract of Preparation Example 1, 'b' represents a fermented ginseng berry *Pleurotus ferulae* product of Example 1, 'c' represents a fermented ginseng berry *Tricholoma matsutake* product of Comparative Example 1, 'd' represents a fermented ginseng berry *Sarcodon aspratus* product of Comparative Example 2, 'e' represents a fermented ginseng berry *Phellinus linteus* product of Comparative Example 3, and 'f' represents a fermented ginseng berry *Ganoderma lucidum* product of Comparative Example 4.

Hereinafter, embodiments of the prevent invention will be described in detail.

Meanwhile, *Panax ginseng* C. A. Meyter used for the present invention which is called "ginseng berry" is the fruit of the 4 years or more old ginseng plant harvested for only about one week in the middle of July. Ginseng berry extracts have been widely utilized in a variety of applications to date. There is no research demonstrating the fact discovered by the present invention that the extract of ginseng berries fermented with *Pleurotus ferulae* exhibits considerably superior anti-oxidation, anti-inflammation, collagen synthesis facilitation, skin wrinkle care, whitening, moisturizing, skin barrier improvement and atopy alleviation effects, as compared to ginseng berry extracts.

Meanwhile, *Pleurotus ferulae Lenzi* is a kind of mushroom which belongs to pleurototaceae and *pleurotus*. *Pleurotus ferulae* is the name given to call to grow in glassroots called "*ferula asafetida*" in Xinjiang, China and has been artificially cultivated since 1983. *Pleurotus ferulae* is known to have been first found in the Madonic Mountain, the Sicily Island, Italy in 1963. *Pleurotus ferulae* is known to be a nutrient repository. *Pleurotus ferulae* having a delicate and soft pine fragrance had been used in China from old times due to potent medical efficacies including treatment of stomach and kidney disorders, cough drop, removal of inflammation and prevention of diseases of obstetrics and gynecology.

The present inventors fermented ginseng berries with a variety of mushrooms as raw materials. As a result, the present inventors discovered that the ginseng berry fermented with *Pleurotus ferulae* mycelium exhibited superior anti-oxidation, anti-inflammation, collagen synthesis facilitation, skin wrinkle care, whitening, moisturizing, skin barrier improvement and atopy alleviation effects. The present invention was completed based on this discovery.

Meanwhile, regarding the cosmetic composition of the present invention, the ginseng berry extract may be prepared using a common solvent in accordance with an ordinary method well-known in the art, that is, under ordinary temperature and pressure conditions. For example, the ginseng berry extract which is the active ingredient of the composition of the present invention may be prepared by extracting ginseng berries using a solvent selected from the group consisting of water, C1-C4 anhydrous or aqueous lower alcohol, acetone, ethyl acetate, butyl acetate and 1,3-butylene glycol, and optionally mixing the extract. The solvent is preferably alcohol, more preferably ethanol, even more preferably, 70% ethanol. The extraction solvent is preferably added in an amount of 1 to 15-fold, more preferably 5 to 10-fold, most preferably 7-fold, of a dry weight of the ginseng berry.

Meanwhile, the fermented ginseng berry *Pleurotus ferulae* product according to the present invention may include an extract obtained by the extraction method described above and an extract obtained by a subsequent common purification process. For example, the fermented ginseng berry *Pleurotus ferulae* product includes fragments obtained by further performing a variety of purification processes such as separation using ultrafiltration membranes having a constant cut-off value and separation using a variety of chromatography (manufactured for separation according to size, charges, and hydrophobicity or hydrophilicity).

In addition, the fermented ginseng berry *Pleurotus ferulae* product according to the present invention may include a fermented product prepared in the form of a powder, obtained by a further process such as distillation under reduced pressure, and lyophilization or spray-drying.

Meanwhile, in a preferred embodiment of the present invention, the content of the fermented ginseng berry *Pleurotus ferulae* product in the cosmetic composition of the present invention is preferably 0.0001 to 100.0% by weight, more preferably 0.001 to 90.0% by weight, most preferably 0.1 to 85.0% by weight, with respect to the total weight of the cosmetic composition.

Meanwhile, as can be seen from the experiment described below, the fermented ginseng berry *Pleurotus ferulae* product according to the present invention superior anti-oxidation effect (see Experimental Example 1), superior anti-inflammatory effect (see Experimental Example 3), superior collagen synthesis effect (see Experimental Example 4), superior wrinkle alleviation effect (see Experimental Example 5), and superior whitening effect (see Experimental Example 6).

It is demonstrated that the cosmetic composition prepared using the fermented ginseng berry *Pleurotus ferulae* product having the effects described above, as an active ingredient, exhibits superior skin moisturizing improvement effect (see Experimental Example 7), superior skin barrier improvement effect (see Experimental Example 8), and superior atopy alleviation effect (see Experimental Example 9).

Meanwhile, the cosmetic composition according to the present invention may have any one formulation selected from the group consisting of solutions, suspensions, emulsions, pastes, gels, creams, lotions, powders, soaps, surfactant-containing cleansings, oils, powder foundations, emulsion foundations, wax foundations and sprays, but the present invention is not necessarily limited thereto.

Meanwhile, the composition of the present invention may further include additives commonly used in cosmetics, such as hydrophilic or lyphophilic gelling agents, hydrophilic or lyphophilic activators, preservatives, antioxidants, solvents, flavoring agents, fillers, blockers, pigments, deodorant agents and dyes. These additives may be present in amounts commonly used in the art and may be for example 0.0001 to 100.0% by weight with respect to the total weight of the cosmetic composition. The additives and contents thereof are selected such that preferred features of the cosmetic composition according to the present invention are not impaired.

EXAMPLE

The present invention will be described in more detail with reference to the following Examples. The scope of the present invention is not limited to the following examples and covers modifications of the technical spirit substantially equivalent thereto.

Preparation Example 1: Preparation of Ginseng Berry Extract

Ginseng berries were washed with distilled water, dried, thoroughly crushed and passed through a 100 mesh sieve. The crushed ginseng berry granules were added to 70% ethanol such that a concentration of the resulting mixture was adjusted to 150 g/L, extracted under reflux for 5 hours three times and then macerated. Then, the resulting product was filtered through Whatman #3 filter paper, concentrated under reduced pressure at 50° C. or less and lyophilized.

Example 1: Preparation of Fermented Ginseng Berry *Pleurotus ferulae* Product 1 to 4% of glucose was added to 5 g of the ginseng berry concentrate prepared in Preparation Example 1, and 0.2 to 0.5% of peptone was further added thereto, followed by sterilization. The sterilized product was inoculated at a concentration of 25 g/L with a *Pleurotus ferulae Lenzi.* strain culture liquid, followed by culturing. The culturing was performed in a 5 L fermenter for 7 days at 37° C. and a pH of 5 to 7. After culturing, the culture solution was centrifuged to primarily remove culture strain and sterilized (121° C., 15 minutes, 1.5 atm) to prevent further culturing.

Ethanol was added to the fermented ginseng berry product obtained by fermentation and then primary removal of culture bacteria so as to obtain a final 70% (V/V) aqueous ethanol solution, extracted under reflux for 5 hours three times, macerated and filtered through Whatman #3 filter paper. After filtering, the resulting extract was concentrated in a concentrator under reduced pressure at 50° C. or less and lyophilized.

Comparative Example 1: Preparation of Fermented Ginseng Berry Tricholoma Matautake Product In Comparative Example 1, the ginseng berry extract obtained in Preparation Example 1 was fermented with *Tricholoma matsutake* mycelium to prepare a fermented ginseng berry *Tricholoma matsutake* product. The present experiment was performed in the same manner as in Example 1 except that *Tricholoma matsutake* was used, instead of *Pleurotus ferulae*.

Comparative Example 2: Preparation of Fermented Ginseng Berry Sarcodon Aspratus Product In Comparative Example 1, the ginseng berry extract obtained in Preparation Example 1 was fermented with *Sarcodon aspratus* mycelium to prepare a fermented ginseng berry *Sarcodon aspratus* product. The present experiment was performed in the same manner as in Example 1 except that *Sarcodon aspratus* was used, instead of *Pleurotus ferulae*.

Comparative Example 3: Preparation of Fermented Ginseng Berry *Phellinus linteus* Product In Comparative Example 1, the ginseng berry extract obtained in Preparation Example 1 was fermented with *Phellinus linteus* mycelium to prepare a fermented ginseng berry *Phellinus linteus* product. The present experiment was performed in the same manner as in Example 1 except that *Phellinus linteus* was used, instead of *Pleurotus ferulae*.

Comparative Example 4: Preparation of Fermented Ginseng Berry *Ganoderma lucidum* Product In Comparative Example 1, the ginseng berry extract obtained in Preparation Example 1 was fermented with *Ganoderma lucidum* mycelium to prepare a fermented ginseng berry *Ganoderma lucidum* product. The present experiment was performed in the same manner as in Example 1 except that *Ganoderma lucidum* was used, instead of *Pleurotus ferulae*.

Experimental Example 1: Evaluation of Antioxidative Activity of Ginseng Berry Extract and Fermented Ginseng Berry Product Using DPPH Method A powder of the ginseng berry extract obtained in Preparation Example 1 and powders of fermented ginseng berry products obtained in Example 1 and Comparative Examples 1 to 4 were suspended in distilled water and free radical scavenging activities thereof were evaluated at different concentrations (0.001%, 0.002%, 0.005%, 0.01%).

The DPPH (2,2-diphenyl-1-picrylhydrazyl) method is used to measure variation in color from absorbance at 540 nm when scavenging DPPH (2,2-Diphenyl-1-picrylhydrazyl) which is a radical whose inhibitors are stable). Samples used for this experiment are shown in the following Table 1 and free radical scavenging activity was measured using the following Equation 1. Epigallocatechin gallate (EGCG) was used as a control group. Epigallocatechin gallate (EGCG, epigallocatechin-3-gallate) is a polyphenol extracted from green tea leaves, which has been found to be a potent antioxidant.

TABLE 1

| Materials | Control group | Blank of control group (Blank of C) | Experimental group (Exp. Group) | Blank of experimental group (Blank of E) |
|---|---|---|---|---|
| A DPPH (MeOH) | 180 µl | (180 µl MeOH) | 180 µl | (180 µl MeOH) |
| B Sample | (20 µl solvent) | (20 µl solvent) | 20 µl | 20 µl |

$$\text{Scavenging activity (\%)} = \frac{[(C-D)-(A-B)]}{(C-D)} \times 100 \quad \text{Equation 1}$$

A: Abs of experimental group
B: Abs of blank of experimental group

C: Abs of control group

D: Abs of blank of control group

Meanwhile, among fermented mushroom products, the fermented *Pleurotus ferulae* product (Example 1) exhibited the highest free radical scavenging activity. As free radical scavenging activity increases, antioxidative activity increases. Accordingly, the fermented ginseng berry *Pleurotus ferulae* product exhibits antioxidative activity higher than the ginseng berry extract.

Meanwhile, as can be seen from the results of FIG. 1, the fermented ginseng berry products (Example 1 and Comparative Examples 1 to 4) exhibited superior free radical scavenging activity at all different concentrations as compared to the ginseng berry extract (Preparation Example 1). In FIG. 1, 'a' represents a ginseng berry extract of Preparation Example 1, 'b' represents a fermented ginseng berry *Pleurotus ferulae* product of Example 1, 'c' represents a fermented ginseng berry *Tricholoma matsutake* product of Comparative Example 1, 'd' represents a fermented ginseng berry *Sarcodon aspratus* product of Comparative Example 2, 'e' represents a fermented ginseng berry *Phellinus linteus* product of Comparative Example 3, and 'f' represents a fermented ginseng berry *Ganoderma lucidum* product of Comparative Example 4.

Experimental Example 2: Evaluation of Effects of Ginseng Berry Extract and Fermented Ginseng Berry Product on Cell Survival Rate Effects of the ginseng berry extract obtained in Preparation Example 1 and the fermented ginseng berry products obtained in Example 1 and Comparative Examples 1 to 4 on cells were measured. The ginseng berry extract powder obtained in Preparation Example 1 and fermented ginseng berry product powders obtained in Example 1 and Comparative Examples 1 to 4 were suspended in distilled water to obtain different concentrations (0.001%, 0.002%, 0.005%, 0.01%) of suspensions and cell survival rates of the suspensions were measured in accordance with the following method.

Cytotoxicty was measured by a Mosmann method which measures cell survival rate using a MTT {3-(4,5-dimethyl-thiazol-2-yl)-2-5-diphenyltetrazolium bromide}reagent.

HDF was seeded at a concentration of $1 \times 10^4$ cells/well on a 96-well plate and cultured under conditions of 37° C. and 5% $CO_2$ for 24 hours. After a culture medium was removed, the HDF was cultured in a medium treated with the sample at different concentrations for 24 hours, and the medium was removed and washed twice with phosphate buffered saline (PBS). MTT was dissolved at a concentration of 5 mg/mL in PBS, 50 L of the resulting MTT solution was added to HDF and HDF was cultured under the conditions of 37° C. and 5% $CO_2$ for 2 hours. 100 L of dimethyl sulfoxide (DMSO) was added to each well, followed by stirring for 10 minutes. Then, absorbance at 40 nm was measured.

As a result of measurement, respective samples did not exhibit cytotoxicty at all concentrations (not shown). This result demonstrates that the fermented ginseng berry *Pleurotus ferulae* product according to the present invention is harmless to human body and has considerably excellent stability.

Experimental Example 3: Evaluation of Anti-Inflammatory Effect (5-Lipoxygenase Inhibitory Activity) of Ginseng Berry Extract and Fermented Ginseng Berry Product The ginseng berry extract obtained in Preparation Example 1 and the fermented ginseng berry products obtained in Example 1 and Comparative Examples 1 to 4 were suspended in distilled water and anti-inflammatory effects thereof were evaluated by performing a 5-lipoxygenase inhibitory activity test under different concentration conditions (0.001%, 0.002%, 0.005%, 0.01%).

Lipoxygenase is an enzyme which produces various chemical mediators involved in inflammatory or allergic reaction in the body. Inhibitors of lipoxygenase cause inhibition of production of a variety of chemical mediators and are thus effective in alleviating allergies. That is, as 5-lipoxygenase inhibitory capacity increases, anti-inflammatory effect increases. In the present experimental example, activity of lipoxygenase may be indicated by peroxide production measured using substrates and enzymes.

The present experiment was performed using samples shown in the following Table 2 and 5-lipoxygenase inhibitory activity was measured using Equation 1. The control group was nordihydroguaiaretic acid (NDGA) which is a potent antioxidant of fats and oils.

TABLE 2

| | Materials | Control group | Blank of control group (Blank of C) | Experimental group (Exp. Group) | Blank of experimental group (Blank of E) |
|---|---|---|---|---|---|
| A | Buffer | 2 mL | 2 mL | 2 mL | 2 mL |
| B | Sample | 20 µl solvent | 20 µl solvent | 20 µl | 20 µl |
| C | Enzyme | 40 µl | — | 20 µl | — |
| D | Substrate | 70 µl | 70 µl | 70 µl | 70 µl |

Figure 2:
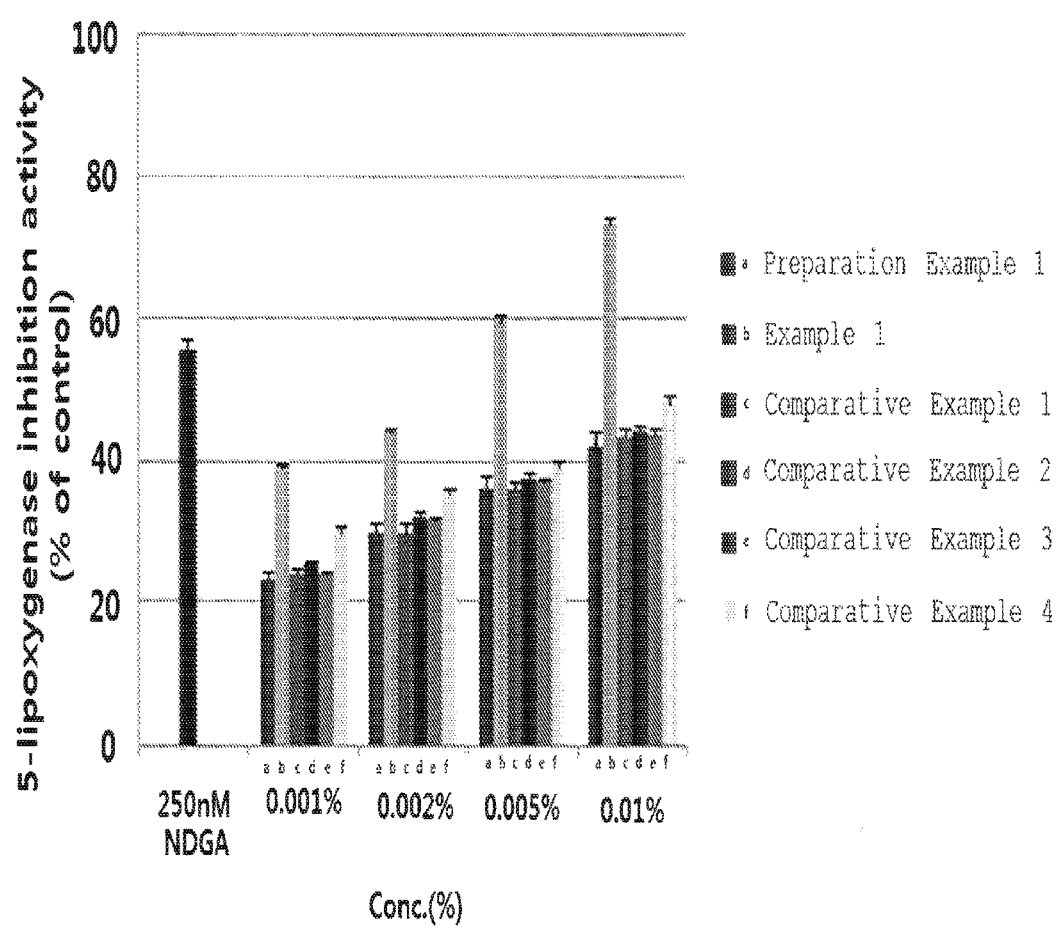
FIG. 2 is a graph showing comparison in 5-lipoxygenase inhibition activity at different concentrations (0.001%, 0.002%, 0.005%, 0.01%) between the ginseng berry extract obtained in Preparation Example 1 and the fermented ginseng berry products obtained in Example 1 and Comparative Examples 1 to 4, wherein 'NDGA' represents nordihydroguaiaretic acid, 'a' represents a ginseng berry extract of Preparation Example 1, 'b' represents a fermented ginseng berry *Pleurotus ferulae* product of Example 1, 'c' represents a fermented ginseng berry *Tricholoma matsutake* product of Comparative Example 1, 'd' represents a fermented ginseng berry *Sarcodon aspratus* product of Comparative Example 2, 'e' represents a fermented ginseng berry *Phellinus linteus* product of Comparative Example 3, and 'f' represents a fermented ginseng berry *Ganoderma lucidum* product of Comparative Example 4.

As can be seen from results shown in FIG. 2, the fermented ginseng berry products of the present invention (Example 1 and Comparative Examples 1 to 4) exhibited superior 5-lipoxygenase inhibitory capacity to the ginseng berry extract (Preparation Example 1). In particular, among the fermented products, the fermented *Pleurotus ferulae* product (Example 1) exhibited the highest 5-lipoxygenase inhibitory capacity and the fermented ginseng berry *Pleurotus ferulae* product exhibited higher anti-inflammatory effects than the ginseng berry extract.

Meanwhile, in FIG. 2, 'a' represents a ginseng berry extract of Preparation Example 1, 'b' represents a fermented ginseng berry *Pleurotus ferulae* product of Example 1, 'c' represents a fermented ginseng berry *Tricholoma matsutake* product of Comparative Example 1, 'd' represents a fermented ginseng berry *Sarcodon aspratus* product of Comparative Example 2, 'e' represents a fermented ginseng berry *Phellinus linteus* product of Comparative Example 3, and 'f' represents a fermented ginseng berry *Ganoderma lucidum* product of Comparative Example 4.

Experimental Example 4: Evaluation of Collagen Synthesis of Ginseng Berry Extract and Fermented Ginseng Berry Product The ginseng berry extract obtained in Preparation Example 1 and the fermented ginseng berry product powders obtained in Example 1 and Comparative Examples 1 to 4 were suspended in distilled water and a collagen biosynthesis increase at different concentrations (0.001%, 0.002%, 0.005%, 0.01%) was evaluated.

Human dermal fibroblasts (HDFs) were seeded on a 24-well plate at a concentration of $5 \times 10^4$ cells/well and cultured under the conditions of 37° C. and 5% $CO_2$ for 24 hours, and were further cultured in serum-free DMEMs (Dulbecco's Modified Eagle's Mediums) containing the ginseng berry extract obtained in Preparation Example 1 and the fermented ginseng berry products obtained in Example 1 and Comparative Examples 1 to 4 and in a serum-free DMEM medium not containing the fermented ginseng berry product and the ginseng berry extract, as a control group. After culturing, the supernatant present on each well was collected, and an amount of procollagen type I C-peptide (PICP) was measured using a collagen kit and was calculated in terms of ng/ml. As a result, an amount of synthesized collagen was measured. Collagen biosynthesis increase (%) was calculated in accordance with the following Equation 2 and L-ascorbic acid (L-AA) having the effect of facilitating collagen synthesis was used as a control group.

Collagen biosynthesis increase (%)=collagen amount of experimental group/collagen amount of control group×100     Equation 2

Figure 3:
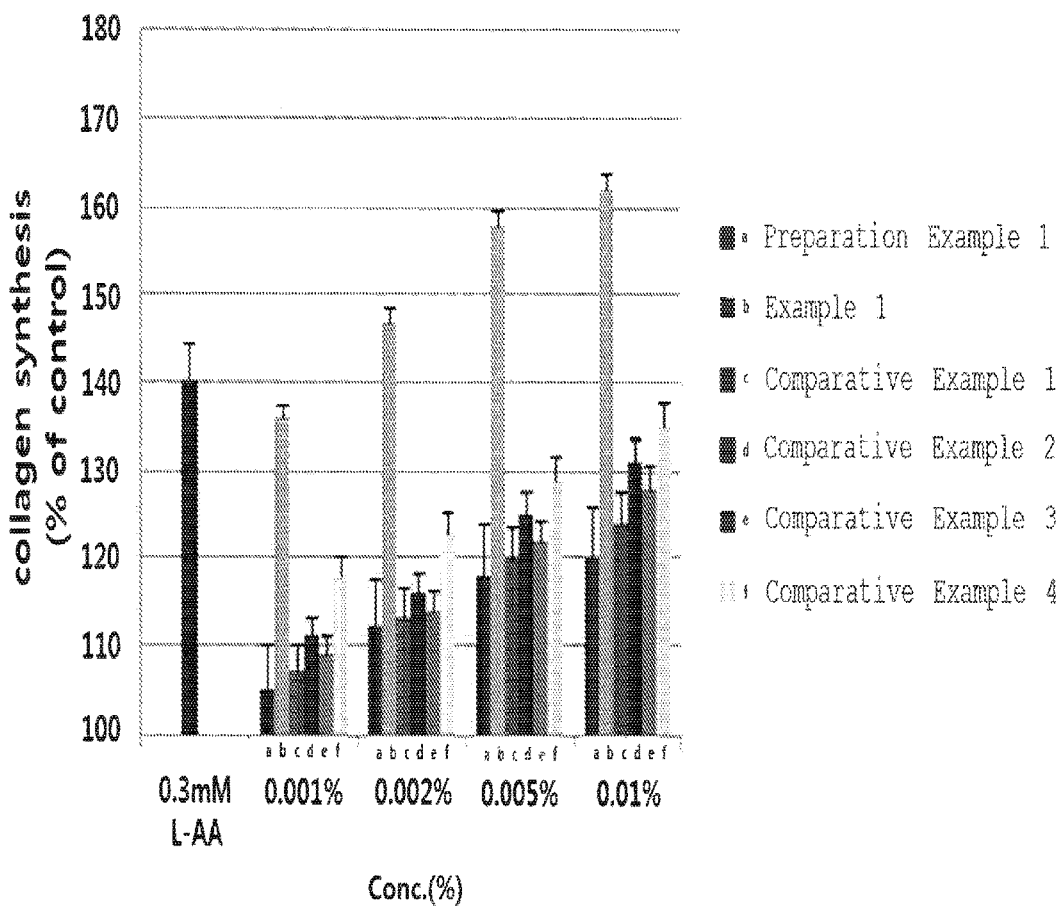
FIG. 3 is a graph showing comparison in collagen synthesis at different concentrations (0.001%, 0.002%, 0.005%, 0.01%) between the ginseng berry extract obtained in Preparation Example 1 and the fermented ginseng berry products obtained in Example 1 and Comparative Examples 1 to 4, wherein 'L-AA' represents L-ascorbic acid, 'a' represents a ginseng berry extract of Preparation Example 1, 'b' represents a fermented ginseng berry *Pleurotus ferulae* product of Example 1, 'c' represents a fermented ginseng berry *Tricholoma matsutake* product of Comparative Example 1, 'd' represents a fermented ginseng berry *Sarcodon aspratus* product of Comparative Example 2, 'e' represents a fermented ginseng berry *Phellinus linteus* product of Comparative Example 3, and 'f' represents a fermented ginseng berry *Ganoderma lucidum* product of Comparative Example 4.

As can be seen from results shown in FIG. 3, the fermented ginseng berry products of the present invention (Example 1 and Comparative Examples 1 to 4) exhibited higher collagen synthesis at all the concentrations than the ginseng berry extract (Preparation Example 1). In particular, among the fermented products, the fermented *Pleurotus ferulae* product (Example 1) exhibited the highest collagen synthesis.

Meanwhile, in FIG. 3, 'a' represents a ginseng berry extract of Preparation Example 1, 'b' represents a fermented ginseng berry *Pleurotus ferulae* product of Example 1, 'c' represents a fermented ginseng berry *Tricholoma matsutake* product of Comparative Example 1, 'd' represents a fermented ginseng berry *Sarcodon aspratus* product of Comparative Example 2, 'e' represents a fermented ginseng berry *Phellinus linteus* product of Comparative Example 3, and 'f' represents a fermented ginseng berry *Ganoderma lucidum* product of Comparative Example 4.

Experimental Example 5: Evaluation of Effects of Ginseng Berry Extracts and Fermented Ginseng Berry Products on Wrinkle Alleviation The ginseng berry extract obtained in Preparation Example 1 and the fermented ginseng berry product powders obtained in Example 1 and Comparative Examples 1 to 4 were suspended in distilled water, and wrinkle alleviation effects at different concentrations (0.001%, 0.002%, 0.005%, 0.01%) were evaluated.

For this experiment, human dermal fibroblasts were irradiated with UVA at an energy of 5 J/cm$^2$ in a UV chamber. Conditions of the dose of ultraviolet radiation and culture time which maximize expression of matrix metalloproteinase (MMP-1) in fibroblasts were established through preliminary testing. A negative control group was wrapped with a foil and exposed to UVA for the same time. Here, UVA dose was measured using a UV radiometer. The cells during irradiation of UVA were cultured in the medium previously used. After UVA irradiation, the cells were cultured in a fresh medium containing samples for 24 hours and 96-well plates were coated with the medium. The cells were treated with primary antibodies (MMP-1 (Ab-5) monoclonal antibody, MMP-1 (Ab-3) monoclonal antibody) and reaction was conducted at 37° C. for 60 minutes. The cells were reacted with anti-mouse IgG (whole mouse, alkaline phosphatase conjugated) as a secondary antibody for about 60 minutes, and were then reacted with an alkaline phosphatase substrate solution (1 mg/mL ρ-nitrophenyl phosphate in diethanolamine buffer solution) at room temperature for 30 minutes, and absorbance at 405 nm was measured using a microplate reader. A control group was not treated with the sample.

Figure 4:
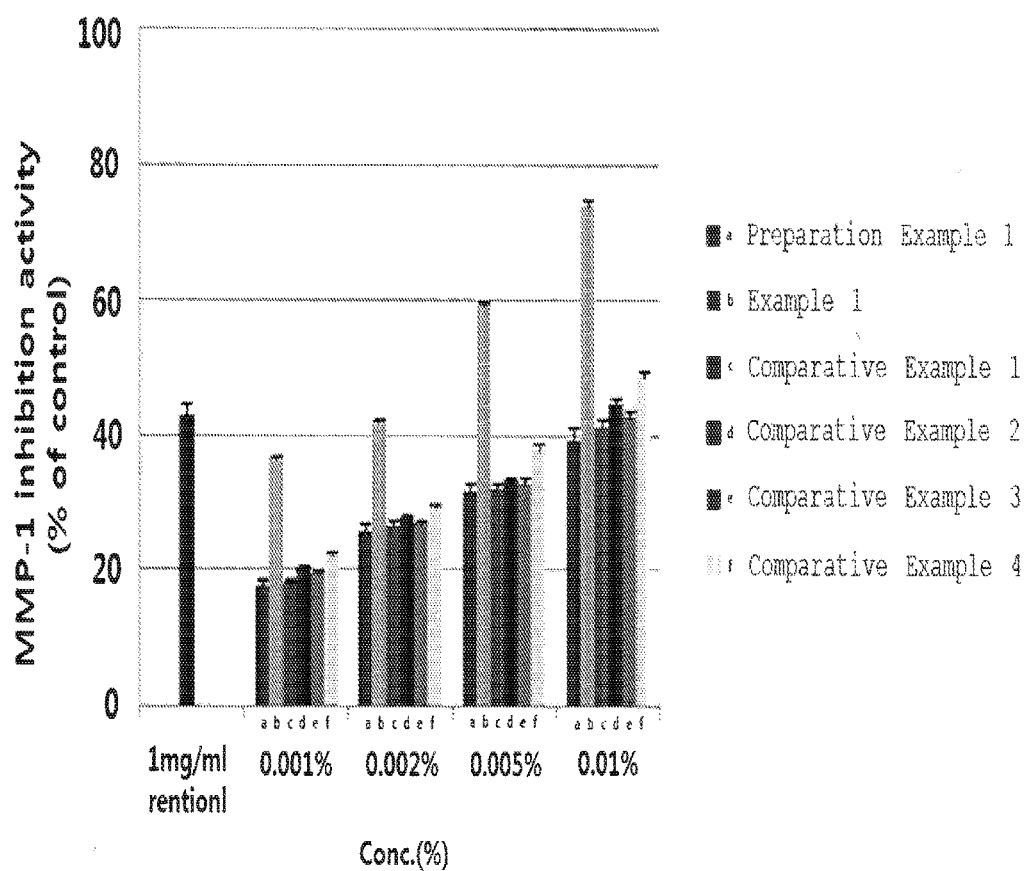
FIG. 4 is a graph showing comparison in MMP-1 inhibition activity at different concentrations (0.001%, 0.002%, 0.005%, 0.01%) between the ginseng berry extract obtained in Preparation Example 1 and the fermented ginseng berry products obtained in Example 1 and Comparative Examples 1 to 4, wherein 'retinol' represents retinol, 'a' represents a ginseng berry extract of Preparation Example 1, 'b' represents a fermented ginseng berry *Pleurotus ferulae* product of Example 1, 'c' represents a fermented ginseng berry *Tricholoma matsutake* product of Comparative Example 1, 'd' represents a fermented ginseng berry *Sarcodon aspratus* product of Comparative Example 2, 'e' represents a fermented ginseng berry *Phellinus linteus* product of Comparative Example 3, and 'f' represents a fermented ginseng berry *Ganoderma lucidum* product of Comparative Example 4.

As can be seen from results shown in FIG. 4, at all concentrations (0.001%, 0.002%, 0.005%, 0.01%), the fermented ginseng berry products of the present invention (Example 1 and Comparative Examples 1 to 4) exhibited superior MMP-1 expression inhibitory capacity to the ginseng berry extract (Preparation Example 1).

In particular, among the fermented products, the fermented *Pleurotus ferulae* product (Example 1) exhibited the highest MMP-1 exhibition inhibitory capacity. Generally, as MMP-1 exhibition inhibitory capacity increases, skin wrinkle alleviation effect increases. Accordingly, the fermented ginseng berry *Pleurotus ferulae* product exhibited superior skin wrinkle alleviation effect to the ginseng berry extract.

Meanwhile, in FIG. 4, 'a' represents a ginseng berry extract of Preparation Example 1, 'b' represents a fermented ginseng berry *Pleurotus ferulae* product of Example 1, 'c' represents a fermented ginseng berry *Tricholoma matsutake* product of Comparative Example 1, 'd' represents a fermented ginseng berry *Sarcodon aspratus* product of Comparative Example 2, 'e' represents a fermented ginseng berry *Phellinus linteus* product of Comparative Example 3, and 'f' represents a fermented ginseng berry *Ganoderma lucidum* product of Comparative Example 4.

Experimental Example 6: Effect of Fermented Ginseng Berry *Pleurotus ferulae* Product on Inhibition of Tyrosinase The following experiment was performed to confirm the effect of a cosmetic containing the fermented ginseng berry *Pleurotus ferulae* product according to the present invention on tyrosinase inhibition. Tyrosinase (EC 1. 14. 18. 1) as an enzyme was dissolved in a 0.05M phosphate buffer (pH 6.5) such that a concentration of 1,100 unit/ml (final 55 unit) was obtained, L-tyrosine ($C_9H_{11}NO_3$, 181.19) as a substrate was dissolved in a 0.1M phosphate buffer (pH 6.5) such that a concentration of 1.5 mM (final 225 uM) was obtained, the resulting solutions were each diluted with 0.1M sodium phosphate buffer (pH 6.5), and reacted (Table 3) and further reacted at 37° C. for 20 minutes, and absorbance at 492 nm was measured using an ELISA reader (enzyme-linked immunosorbent assay). Kojic acid, which has effects of inhibiting tyrosinase activity and inhibiting production of melanine, was used as a control group.

TABLE 3

| Material | Control group | Blank of control group (Blank of C) | Experimental group (Exp. Group) | Blank of experimental group (Blank of E) |
|---|---|---|---|---|
| A Buffer | 140 μl | 150 μl | 140 μl | 150 μl |
| B Sample | (20 μl solvent) | (20 μl solvent) | 20 μl | 20 μl |
| C Enzyme | 10 μl | — | 10 μl | — |
| D Substrate | 30 μl | 30 μl | 30 μl | 30 μl |

$$\text{Inhibition (\%)} = \frac{[(C-D)-(A-B)]}{(C-D)} \times 100 \quad \text{Equation 3}$$

A: Abs of experimental group
B: Abs of blank of experimental group

C: Abs of control group

D: Abs of blank of control group

Figure 5:
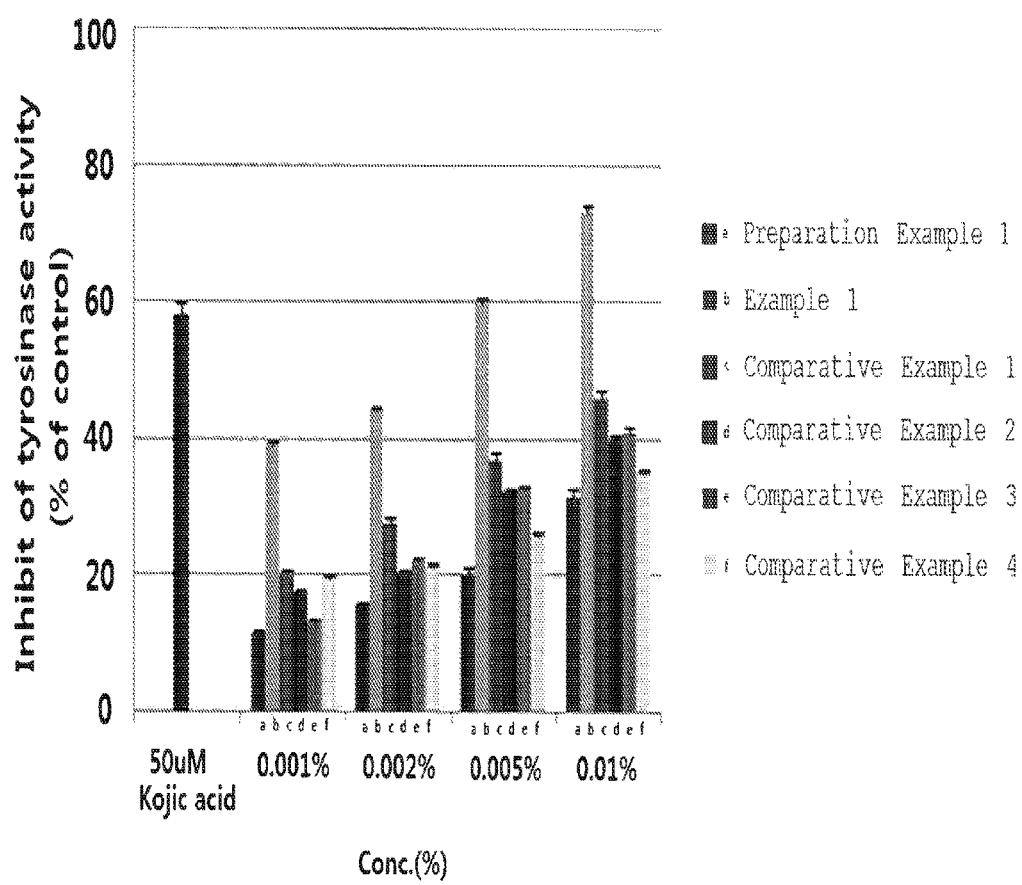
FIG. 5 is a graph showing comparison in inhibition of tyrosinase activity at different concentrations (0.001%, 0.002%, 0.005%, 0.01%) between the ginseng berry extract obtained in Preparation Example 1 and the fermented ginseng berry products obtained in Example 1 and Comparative Examples 1 to 4, wherein 'Kojic acid' represents kojic acid, 'a' represents a ginseng berry extract of Preparation Example 1, 'b' represents a fermented ginseng berry *Pleurotus ferulae* product of Example 1, 'c' represents a fermented ginseng berry *Tricholoma matsutake* product of Comparative Example 1, 'd' represents a fermented ginseng berry *Sarcodon aspratus* product of Comparative Example 2, 'e' represents a fermented ginseng berry *Phellinus linteus* product of Comparative Example 3, and 'f' represents a fermented ginseng berry *Ganoderma lucidum* product of Comparative Example 4.

As can be seen from results shown in FIG. 5, at all concentrations (0.001%, 0.002%, 0.005%, 0.01%), the fermented ginseng berry products of the present invention (Example 1 and Comparative Examples 1 to 4) exhibited superior tyrosinase inhibitory capacity to the ginseng berry extract (Preparation Example 1).

In particular, among the fermented products, the fermented ginseng berry *Pleurotus ferulae* product exhibited superior tyrosinase inhibition effect (whitening effect) to the ginseng berry extract.

Tyrosinase (EC 1.14.18.1) is an important enzyme which performs multiple enzymatic functions in the melanosynthetic pathway. In general, as tyrosinase inhibitory capacity increases, effects associated with skin whitening and propagation inhibition of melanoma formed by malignant alteration of melanine cells increase.

Meanwhile, in FIG. 5, 'a' represents a ginseng berry extract of Preparation Example 1, 'b' represents a fermented ginseng berry *Pleurotus ferulae* product of Example 1, 'c' represents a fermented ginseng berry *Tricholoma matsutake* product of Comparative Example 1, 'd' represents a fermented ginseng berry *Sarcodon aspratus* product of Comparative Example 2, 'e' represents a fermented ginseng berry *Phellinus linteus* product of Comparative Example 3, and 'f' represents a fermented ginseng berry *Ganoderma lucidum* product of Comparative Example 4.

Formulation Example 1 and Formulation Comparative Example 1: Preparation of Cosmetic Containing Fermented Ginseng Berry *Pleurotus ferulae* Product A cosmetic composition containing 30.0% by weight of the fermented ginseng berry *Pleurotus ferulae* product obtained in Example 1 was prepared under the composition conditions shown in the following Table 4 and was referred to as "Formulation Example 1", and a cosmetic composition not containing the fermented ginseng berry *Pleurotus ferulae* product was prepared and referred to as "Formulation Comparative Example 1".

TABLE 4

| Ingredients | Content of formulation Example 1 (wt %) | Content of Formulation Comparative Example 1 (wt %) |
|---|---|---|
| Preparation Example 1 | — | 30.0 |
| Example 1 | 30.0 | — |
| 1,3-BG | 10.0 | 10.0 |
| Glycerine | 5.1 | 5.1 |
| Propylene glycol | 4.2 | 4.2 |
| Tocopheryl acetate | 3.0 | 3.0 |
| Liquid paraffin | 4.6 | 4.6 |
| Triethylamine | 1.0 | 1.0 |
| Squalane | 3.1 | 3.1 |
| Macadamia nut oil | 2.5 | 2.5 |
| Polysorbate 60 | 1.6 | 1.6 |
| Sorbitan sequoleate | 1.6 | 1.6 |
| Propyl paraben | 0.6 | 0.6 |
| Carboxyvinyl polymer | 1.5 | 1.5 |
| Flavor | Trace | Trace |
| preservative | Trace | Trace |
| Distilled water | Balance | Balance |
| Total | 100 | 100 |

Experimental Example 7: Effect of Fermented Ginseng Berry *Pleurotus ferulae* Product on Improvement of Skin Moisturizing The following experiment was performed in order to confirm the effect of the cosmetic containing the fermented ginseng berry *Pleurotus ferulae* product according to the present invention on improvement of skin moisturizing power.

40 subjects in their 20s to 40s who have no skin diseases were divided into two groups, each group having 20 subjects, a nutrient cream of Formulation Example 1 and a nutrient cream of Formulation Comparative Example 1 were applied over the entire region of the face twice per day for one month. Prior to application, skin conductance was measured using a corneometer (CM820 courage Khazaka electronic GmbH, Germany) under constant temperature and humidity conditions (24° C., humidity 40%) and was set to a reference value, skin conductance increase (%) was measured after one, two and four weeks, and increases thereof were evaluated. The results are shown in the following Table 5.

TABLE 5

| Items | After one week | After two weeks | After four weeks |
|---|---|---|---|
| Formulation Example 1 | 55 | 59 | 64 |
| Formulation Comparative Example 1 | 26 | 30 | 36 |

(Unit: %)

As a result of the experiment, Formulation Example 1, the cosmetic containing the fermented ginseng berry *Pleurotus ferulae* product according to the present invention exhibited a considerably high skin conductance increase, as compared to Formulation Comparative Example 1. In general, skin conductance increases in proportion to skin water content, the cosmetic containing the fermented ginseng berry *Pleurotus ferulae* product according to the present invention maintained high skin water content, as compared to a cosmetic not containing the fermented ginseng berry *Pleurotus ferulae* product (not shown).

Experimental Example 8: Effect of Fermented Ginseng Berry *Pleurotus ferulae* Product on Improvement of Skin Barrier Function The following experiment was performed in order to confirm the effect of the cosmetic containing the fermented ginseng berry *Pleurotus ferulae* product according to the present invention on improvement of skin barrier.

In the present experimental example, transepidemal water losses (TEWL) of humans to whom the cosmetic of Formulation Example 1 and the cosmetic of Formulation Comparative Example 1 were applied were measured using a Tewameter (TM300, Courage and Khazaka Electronic Co., Germany) and were then compared. The samples were applied to the right and left sides of faces of 40 women in their 20s to 40s, transepidemal water loss of an area spaced 3 cm apart to the right and 1 cm apart downward from the eye site was measured three times using Tewameter (TM300, Courage and Khazaka Electronic Co., Germany) before application and 1 hour, 2 hours, 4 hours and 6 hours after application and an average of three transepidemal water loss values was calculated.

TABLE 6

| Items | 1 hour | 2 hours | 4 hours | 6 hours |
|---|---|---|---|---|
| Formulation Example 1 | 15.5 | 14.6 | 12.2 | 9.2 |
| Formulation Comparative Example 1 | 18.1 | 16.9 | 13.8 | 11.2 |

(Unit: $g/h/m^2$)

As a result of measurement of transepidemal water loss, as can be seen from Table 6, transepidemal water loss on the facial skin of subjects to whom the cream prepared in Formulation Example 1 was applied was decreased. This result demonstrated that the cosmetic containing the fermented ginseng berry *Pleurotus ferulae* product according to the present invention exhibited superior skin barrier improvement effect, as compared to cosmetics not containing the fermented ginseng berry *Pleurotus ferulae* product (not shown).

Experimental Example 9: Effect of Fermented Ginseng Berry *Pleurotus ferulae* Product on Atopy Alleviation The following experiment was performed in order to confirm the effect of the cosmetic containing the fermented ginseng berry *Pleurotus ferulae* product according to the present invention on atopy alleviation. Among 20 subjects (3-40 olds) who suffered from atopy, the cream of Formulation Example 1 and the cream of Formulation Comparative Example 1 were continuously applied to the atopy skin site of 10 subjects and the remaining 10 subjects, respectively, twice per day over four weeks. Atopy dermatitis severity (0 point: none, 10 point: weak, 20 point: mild, 30 point: sever, 40 point: extremely sever), IgE variation, eosinophil variation, water content and skin acidity on the test site of the subjects were measured before application of the product (0 week) and at four weeks after application of the product. All the subjects who participated in the experiment had no abnormal response.

The following Table 7 shows comparison in atopy alleviation between subjects treated with creams prepared in Formulation Example 1 and Formulation Comparative Example 1.

TABLE 7

| Items | Atopy dermatitis severity (point) | | IgE variation (mg/dl) | | Eosinophil variation (ea) | | Water content ($g/cm^2h$) | | Skin acidity (pH) | |
|---|---|---|---|---|---|---|---|---|---|---|
| | Before | After | Before | After | Before | After | Before | After | Before | After |
| Formulation Example 1 | 37.41 | 28.12 | 435.9 | 321.4 | 317 | 249 | 25.84 | 26.57 | 5.719 | 6.071 |
| Formulation Comparative Example 1 | 37.68 | 31.53 | 443.7 | 363.8 | 321 | 275 | 26.31 | 25.11 | 5.717 | 5.833 | n = 20,
p < 0.05

As a result of the experiment, subjects to whom the cream containing the fermented ginseng berry *Pleurotus ferulae* product of Formulation Example 1 was applied were excellent in terms of atopy dermatitis severity as atopy skin diagnostic criteria, variation in IgE and eosinophil in blood, water content and improvement in skin acidity. The cosmetic containing the fermented ginseng berry *Pleurotus ferulae* product according to the present invention exhibited superior atopy alleviation to cosmetics not containing the fermented ginseng berry *Pleurotus ferulae* product (not shown).

As apparent from the fore-going, the fermented ginseng berry *Pleurotus ferulae* product according to the present invention exhibits considerably superior anti-oxidation, anti-inflammation, collagen synthesis facilitation, skin wrinkle care, whitening, moisturizing, skin barrier improvement and atopy alleviation effects, as compared to a ginseng berry extract.

Accordingly, the present invention also provides a cosmetic composition having superior functionality.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing a cosmetic composition comprising an effective amount of a fermented ginseng berry extract, comprising:
    (a) extracting ginseng berries with an extraction solvent to produce a ginseng berry extract;
    (b) inoculating the ginseng berry extract with *Pleurotus ferulae*;
    (c) culturing the inoculated ginseng berry extract in a fermenter apparatus to obtain a fermented ginseng berry extract; and
    (d) combining an effective amount of the fermented ginseng berry extract with a cosmetically acceptable carrier to obtain the cosmetic composition.

2. The method of claim 1, wherein the extraction solvent is selected from the group consisting of: water, $C_1$-$C_4$ anhydrous or aqueous lower alcohol, acetone, ethyl acetate, butyl acetate, and 1,3-butylene glycol.

3. The method of claim 1, wherein the fermented ginseng berry extract is an amount of about 0.0001% to about 100.0% by weight based on the total weight of the cosmetic composition.

4. The method of claim 1, wherein the ginseng berry extract is inoculated with *Pleurotus* ferulae at a concentration of 25 g/L.

5. The method of claim 1, wherein the culturing is performed in a fermenter apparatus at 37° C. and a pH of 5 to 7.

6. The method of claim 1, wherein the effective amount of fermented ginseng berry extract promotes one or more skin beneficial effects selected from the group consisting of: anti-oxidation, anti-inflammation, anti-wrinkles, skin whitening, skin moisturizing, improving skin barrier function or collagen synthesis, and atopy alleviation.

* * * * *